United States Patent
Yanai et al.

(10) Patent No.: US 8,968,174 B2
(45) Date of Patent: Mar. 3, 2015

(54) MOTOR FAULT MONITOR FOR IMPLANTABLE BLOOD PUMP

(71) Applicant: Thoratec Corporation, Pleasanton, CA (US)

(72) Inventors: Masamichi Yanai, Ann Arbor, MI (US); Tao Zhang, Ann Arbor, MI (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/742,469

(22) Filed: Jan. 16, 2013

(65) Prior Publication Data

US 2014/0200389 A1 Jul. 17, 2014

(51) Int. Cl.
*A61M 1/12* (2006.01)
*A61M 1/10* (2006.01)

(52) U.S. Cl.
CPC .......... *A61M 1/1086* (2013.01); *A61M 2205/17* (2013.01)
USPC ............................................. 600/16; 623/3.1

(58) Field of Classification Search
CPC ...... A61M 1/10; A61M 1/127; A61M 1/1086
USPC ............................................. 600/16; 623/3.1
See application file for complete search history.

(56) References Cited

U.S. PATENT DOCUMENTS

| | | | |
|---|---|---|---|
| 4,434,389 A * | 2/1984 | Langley et al. ......... 318/400.41 |
| 5,613,935 A | 3/1997 | Jarvik | |
| 5,630,836 A | 5/1997 | Prem et al. | |
| 5,843,129 A | 12/1998 | Larson et al. | |
| 5,917,295 A | 6/1999 | Mongeau | |
| 6,149,683 A | 11/2000 | Lancisi et al. | |
| 6,320,731 B1 | 11/2001 | Eaves et al. | |
| 6,351,048 B1 | 2/2002 | Schob et al. | |
| 6,605,032 B2 | 8/2003 | Benkowski et al. | |
| 7,660,635 B1 | 2/2010 | Verness et al. | |
| 2004/0145337 A1 | 7/2004 | Morishita | |
| 2004/0263341 A1 | 12/2004 | Enzinna | |
| 2005/0073273 A1 | 4/2005 | Maslov et al. | |
| 2008/0007196 A1 | 1/2008 | Tan et al. | |
| 2008/0211439 A1 | 9/2008 | Yokota et al. | |
| 2010/0305692 A1 | 12/2010 | Thomas et al. | |
| 2011/0015732 A1 | 1/2011 | Kanebako | |
| 2011/0218383 A1 | 9/2011 | Broen et al. | |
| 2011/0218384 A1 | 9/2011 | Bachman et al. | |
| 2011/0218385 A1 | 9/2011 | Bolyard et al. | |
| 2013/0289334 A1 * | 10/2013 | Badstibner et al. ............. 600/16 |

FOREIGN PATENT DOCUMENTS

WO 9414226 6/1994

OTHER PUBLICATIONS

International Search Report and Written Opinion in PCT/US2014/011786 mailed on May 5, 2014, 11 pages.

* cited by examiner

*Primary Examiner* — Joseph Dietrich
(74) *Attorney, Agent, or Firm* — Kilpatrick Townsend & Stockton LLP

(57) ABSTRACT

A implantable pump system comprises an implantable pump motor and an external unit. An inverter comprises respective phases couple to the motor via a cable with redundant conductors for each phase. A controller receives power measurements for all the redundant conductors, which are combined and compared in order to detect failures in the non-redundant components within the motor and windings.

17 Claims, 3 Drawing Sheets

MOTOR FAULT MONITOR FOR IMPLANTABLE BLOOD PUMP

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices, and, more specifically, to enhanced reliability and fault monitoring of motor components of an implanted pump unit.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated into the pump), drive electronics, microprocessor control unit, and an energy source such as rechargeable batteries and/or an AC power conditioning circuit. The system may be implantable, either fully or partially. The goal of the control unit is to autonomously control the pump performance to satisfy the physiologic needs of the patient while maintaining safe and reliable system operation. A control system for varying pump speed to achieve a target blood flow based on physiologic conditions is shown in U.S. Pat. No. 7,160,243, issued Jan. 9, 2007, which is incorporated herein by reference in its entirety. Thus, a target blood flow rate may be established based on the patient's heart rate so that the physiologic demand is met. The control unit may establish a speed setpoint for the pump motor to achieve the target flow. Whether the control unit controls the speed setpoint in order to achieve flow on demand or whether a pump speed is merely controlled to achieve a static flow or speed as determined separately by a physician, it is essential to automatically monitor pump performance to ensure that life support functions are maintained.

A typical pump motor employed for a blood pump is a three-phase permanent magnet electric motor that can be driven as a brushless DC or a synchronous AC motor without any position sensor. The need for a position sensor is avoided by controlling motor operation with one of a variety of methods that use the measured stator phase currents to infer the position. Vector control is one typical method used in variable frequency drives to control the torque and speed of a three-phase electric motor by controlling the current fed to the motor phases. This control can be implemented using a fixed or variable voltage drive delivered via an inverter comprised of pulse width modulated H-bridge power switches arranged in phase legs. Reliability, fault detection, and fault tolerance are important characteristics of an electrically-powered blood pump, drive system, and cable, and it would be desirable to improve each of them.

Co-pending application Ser. No. 13/418,447, filed Mar. 13, 2012, entitled "Fault Monitor For Fault Tolerant Implantable Pump," which is hereby incorporated by reference, discloses a fault-tolerant inverter/cable system wherein redundant inverter legs are coupled to the motor phases by redundant, parallel conductors between the external unit and the implanted pump. For a three-phase motor, the redundant interconnect system includes six conductors in the cable. By monitoring the equality of the current and/or voltage of the two conductors on the same phase, a fault or impending fault can be detected for each individual conductor. However, this system redundancy does not continue into the motor phases and other components within the motor because of size and other limitations. In the event of a failure or degraded condition inside the pump motor (e.g., a soldering terminal failure, a coil wire breakage, damage to a flex circuit substrate, a coil turn-to-turn short, a layer-to-layer short, or a core/yoke detachment), the current/voltage on the conductors for a single phase remain about equal and no fault is detected. Therefore, further means of fault detection would be desirable.

SUMMARY OF THE INVENTION

In one aspect of the invention, a blood pump system for left ventricle assist comprises an implantable pump unit having a multiphase brushless motor including windings for energizing according to first, second, and third phases. A subcutaneous cable has first, second, and third parallel pairs of redundant conductors, wherein the conductor pairs are connected to respective ends of the windings. An external unit is coupled to the cable comprising an H-bridge inverter having first, second, and third phase legs coupled to the first, second, and third conductor pairs, respectively. First and second pairs of power sensors are responsive to electrical power in each of the redundant conductors in the first and second conductor pairs, respectively. A controller is coupled to the H-bridge inverter and the power sensors for 1) switching the H-bridge inverter in a sequence for operating the motor, 2) characterizing a first power utilization parameter of one of the conductor pairs during energization of the first phase, 3) characterizing a second power utilization parameter of one of the conductor pairs during energization of the second phase, 4) characterizing a third power utilization parameter of one of the conductor pairs during energization of the third phase, and 5) pairwise comparing the power utilization parameters and detecting a fault in the implantable pump in response to an imbalance of one of the comparisons.

DETAILED DESCRIPTION OF PREFERRED EMBODIMENTS

Figure 1:
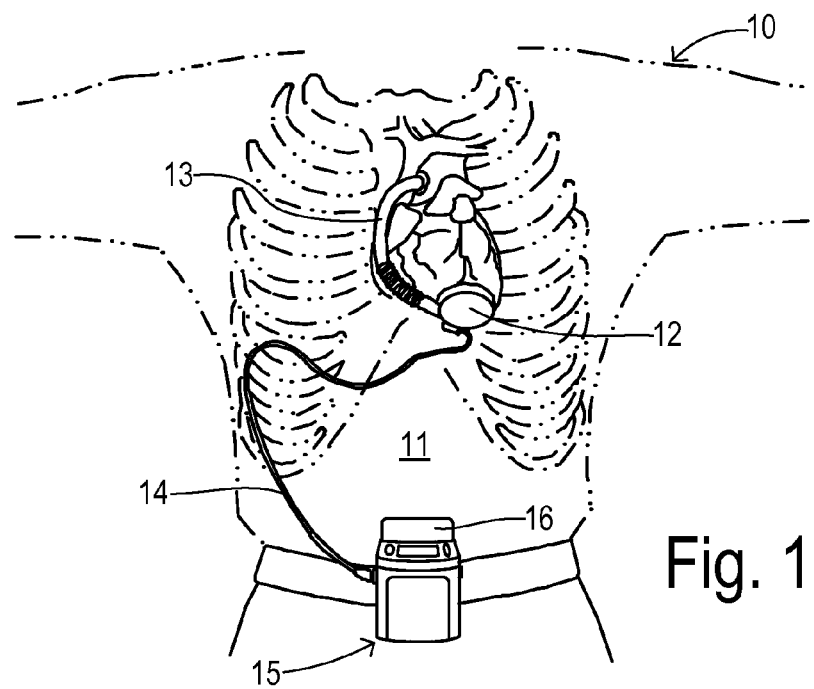
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A subcutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery.

Cable 14 is flexible in order to allow freedom of movement of the patient. Such movement, however, causes stresses to cable 14 and to its connections with pumping unit 12 and control unit 15. To increase reliability and fault tolerance, the present invention uses redundant conductors in cable 14 to supply each of the phase currents that drive the pump motor.

Figure 2:
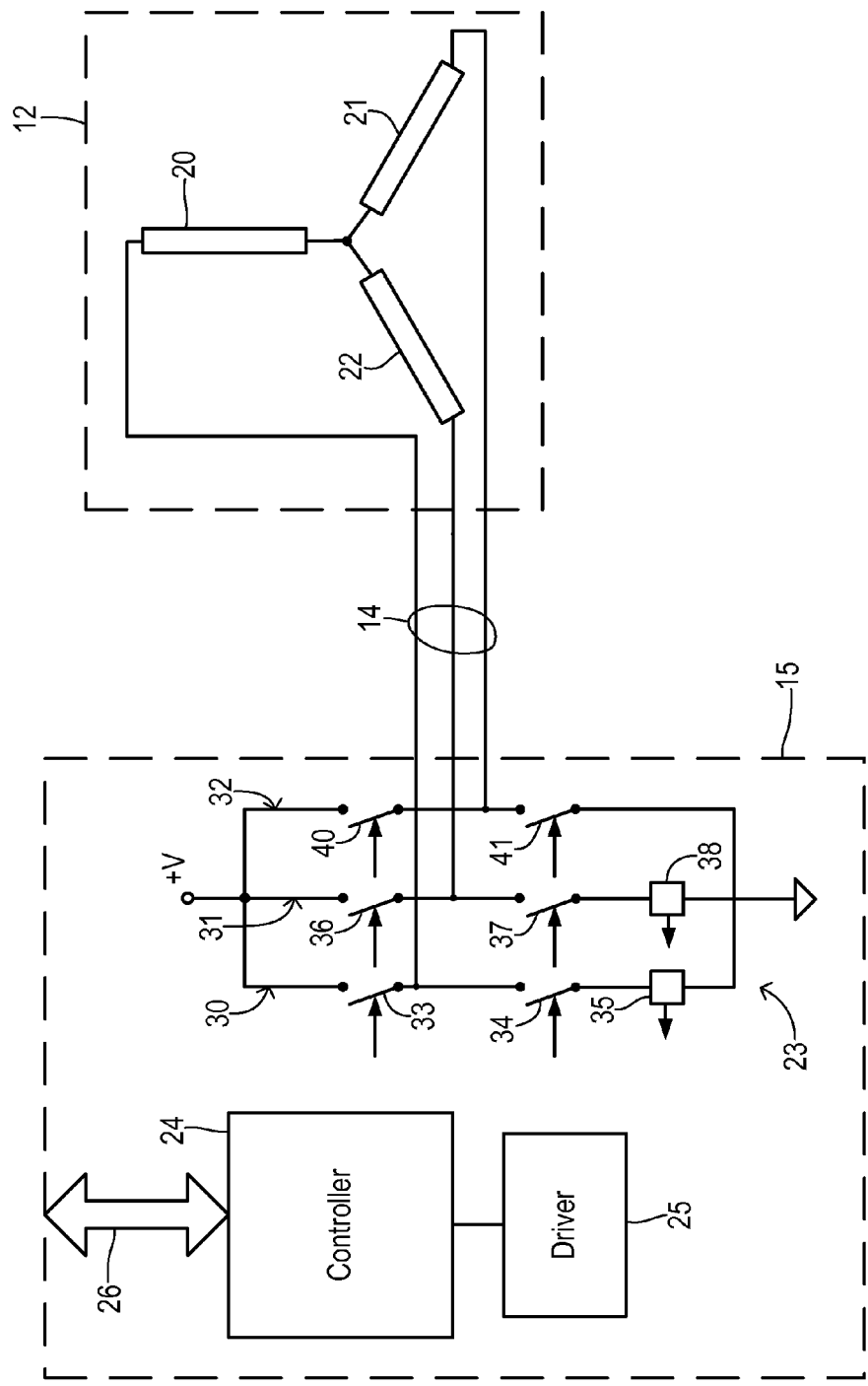
FIG. 2 is a schematic diagram showing a ventricular assist system employing an H-bridge inverter and a controller.

A conventional inverter and cabling for an LVAD system is shown in FIG. 2. A brushless DC motor in pump unit 12 has phase windings 20-22 connected by cable 14 to an H-bridge inverter 23. A controller 24, such as a general purpose microcontroller, implements a field-oriented control (i.e., vector control) or other algorithm to determine proper energization of phase windings 20-22 to obtain the desired motor operation. Controller 24 is connected to a driver 25 for generating drive signals coupled to the control inputs of individual switches (e.g., transistors) in inverter 23. Controller 24 has an input/output 26 for sending messages or generating fault alarms directed at the user or a physician, for example.

Inverter 23 has an H-bridge configuration with a first phase leg 30, a second phase leg 31, and a third phase leg 32. Phase leg 30 has an upper switch 33 and a lower switch 34 which are turned on and off by controller 24 via driver 25 as known in the art. A current sensor 35 in series with phase leg 30 provides a measured current to controller 24 as an input to the vector control algorithm. Similarly, phase leg 31 includes switches 36 and 37 and a current sensor 38. Phase leg 32 includes switches 40 and 41, but a current sensor may not be required since the vector control algorithm can infer a third current based on measured currents from sensors 35 and 38.

Figure 3:
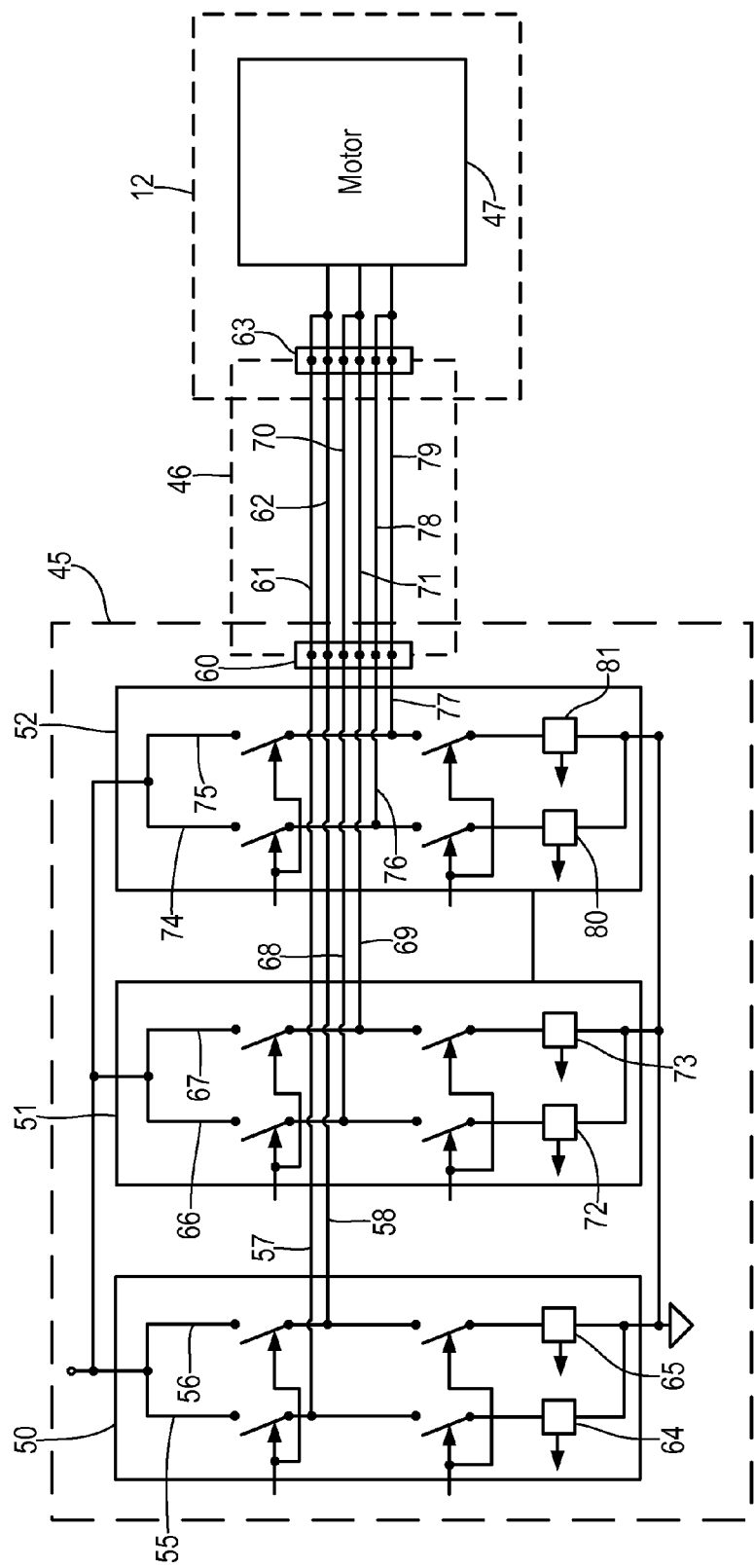
FIG. 3 is a schematic diagram showing redundant phase legs and cable conductors employed in one embodiment of the present invention.

FIG. 3 shows an improved ventricular assist system having higher reliability and fault tolerance as a result of redundant cable conductors and redundant phase legs. Controller 24 and driver 25 are modified for the redundancies and to perform additional fault detection functions as described below. An inverter 45 is coupled by a redundant cable 46 to motor 47 in pump unit 12. Inverter 45 has a first phase 50, a second phase 51, and a third phase 52. First phase 50 has a first phase leg 55 and a second phase leg 56. The upper and lower power switches in legs 55 and 56 are respectively coupled together to provide synchronous operation of the legs. Respective conductors 57 and 58 connect phase legs 55 and 56 to a connector terminal 60. Cable 46 includes conductors 61 and 62 connected at terminal 60 to conductors 57 and 58, respectively. Conductors 61 and 62 are coupled to motor 47 via a terminal connector 63 in pump unit 12. Redundant conductors 61 and 62 become interconnected within pump unit 12 in order to drive a respective winding of motor 47.

Legs 55 and 56 include respective current sensors 64 and 65 measuring the separate current magnitudes flowing in each of legs 55 and 56 (which is also the current flowing in redundant conductors 57 and 58, respectively). The measured currents are coupled to the controller for monitoring and motor control purposes as explained below. In addition to (or instead of) current, a different parameter of the electrical power utilization could be sensed, such as voltage.

Phases 51 and 52 of inverter 45 have an identical configuration. Thus, phase 51 includes redundant phase legs 66 and 67, which are independently connected to terminal 60 by conductors 68 and 69. Corresponding conductors 70 and 71 are provided in cable 46. Current sensors 72 and 73 provide measured currents for phase leg 66 and 67 to the controller. Phase 52 includes legs 74 and 75 having their outputs connected to terminal 60 by conductors 76 and 77. Cable 46 includes conductors 78 and 79 which connect conductors 76 and 77 to pump unit terminal 63. Phase 52 includes current sensors 80 and 81 in legs 74 and 75, respectively, which provide measured currents for legs 74 and 75 to the controller.

The redundancy of the cable conductors, phase leg switches, and phase leg conductors provide fault tolerance whereby damage such as loss of continuity in one conductor or failure of one switch does not prevent operation of the ventricle assist system. Upon failure of one of these, the redundant conductor or phase leg carries the full current load instead of being distributed between the redundant elements, thereby providing continuous operation of the pump.

Prior application Ser. No. 13/418,447 discloses fault monitoring performed by comparing measured currents within redundant phase legs such that, if the currents are substantially equal (indicating that operation of electrical components is the same in each redundant leg) then conditions are nominal and no fault is detected. If the measured currents of a redundant conductor pair are substantially unequal, on the other hand, then a fault is detected. The fault occurrence may trigger an alarm to inform a user that steps should be taken to remedy the fault. However, regular pump operation is maintained by virtue of the redundant element continuing to supply the proper current to the motor.

Figure 4:
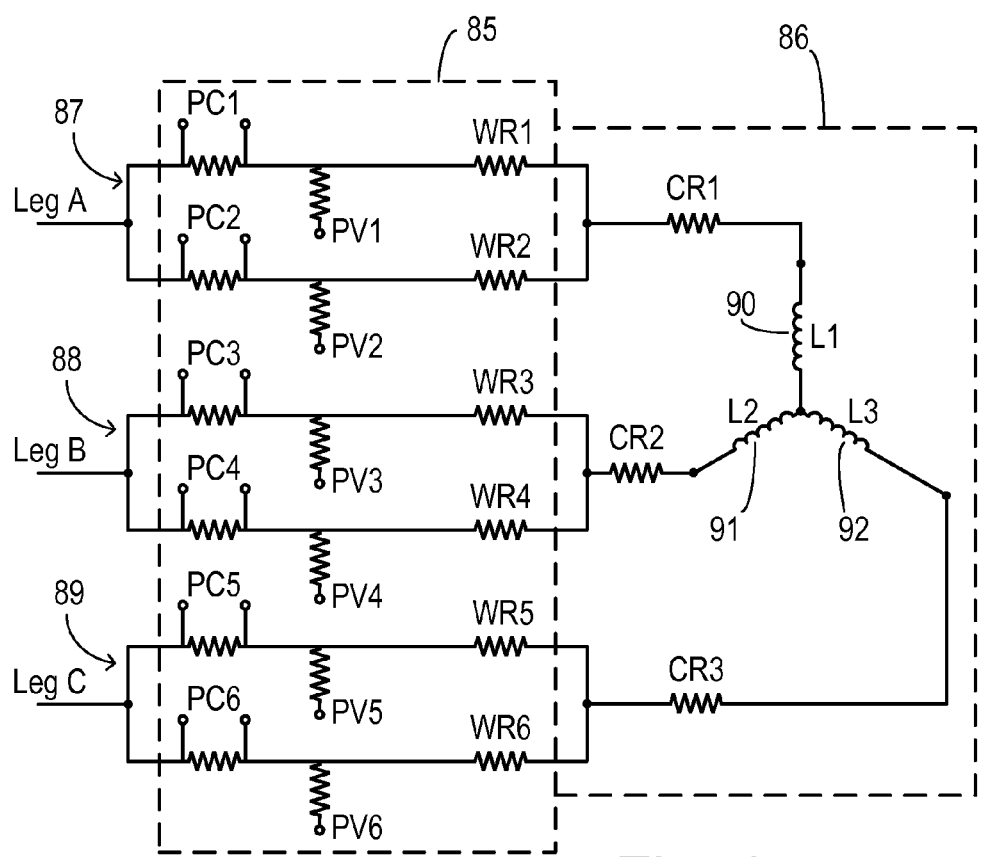
FIG. 4 is an equivalent circuit of lumped resistances and inductances modeling the cable and motor of the present invention.

FIG. 4 shows an equivalent circuit including a redundant cable 85 and pump motor 86. A first redundant conductor pair 87 is driven from an inverter leg A and is coupled to a first winding 90. A second redundant conductor pair 88 is driven from an inverter leg B and is coupled to a second winding 91. A third redundant conductor pair 89 is driven from an inverter leg C and is coupled to a third winding 92. Windings 90-92 are driven in pairs to provide the three phases of the motor operation, which may follow a field-oriented control algorithm.

In a first conductor 93 of first pair 87, power being utilized from leg A is sensed by a current sensor PC1 (phase current 1) and/or a voltage sensor PV1 (phase voltage 1). In a second conductor 94 of first pair 87, power being utilized from leg B is sensed by a current sensor PC2 (phase current 2) and/or a voltage sensor PV2 (phase voltage 2). Conductors 93 and 94 include wire resistances WR1 and WR2 which are both very small and about equal as long as there are no conductor failures. Within motor 86, winding 90 has an inductance L1. A corresponding coil resistance CR1 is likewise small as long as there are no component failures within motor 86 associated with winding 90.

Second and third conductor pairs 88 and 89 include similar sensors and resistances, as indicated using consistent notations. Second winding 91 has an inductance L2 and associated coil resistance CR2. Third winding 92 has an inductance L3 and associated coil resistance CR3. In the absence of failures in motor 86, inductances L1-L3 and resistances CR1-CR3 are each about equal. Therefore, any chosen power utilization parameter that is monitored from cycle to cycle of motor operation will be about the same from phase to phase when no faults are present. By checking for differences (i.e., imbalances) from phase to phase, a fault can be detected using the present invention. Since faults within the motor would affect the individual conductors within a particular pair equally, comparing measured values for one conductor versus the other would not detect a fault. When checking for imbalances between different conductor pairs, it is preferable to include both conductors of a redundant pair together in quantifying a particular phase. Either a sum or average of the power measurement can be used, for example. Although sensors for characterizing power utilization are shown in all three conductor pairs, it should be noted that sensors are only required in two conductor pairs since power in the third can be inferred based on the other two.

If coil resistance CR1 begins to increase (e.g., resulting from a soldering terminal issue, wire breakage, or substrate damage), current for the phases in which winding 90 is energized will begin to decrease compared to the other phases. If inductance L1 begins to decrease (e.g., resulting from a shorted turn in the coil or a detachment of the core/yoke) then a phase voltage may decrease as compared to the other phases. Therefore, the illustrated embodiment of the present invention with redundant cabling adapts the motor controller to perform the steps of 1) switching the H-bridge inverter in a sequence for operating the motor, 2) characterizing a first power utilization parameter of one of the conductor pairs during energization of the first phase, 3) characterizing a second power utilization parameter of one of the conductor pairs during energization of the second phase, 4) characterizing a third power utilization parameter of one of the conductor pairs during energization of the third phase, and 5) pairwise comparing the power utilization parameters and detecting a fault in the implantable pump in response to an imbalance of one of the comparisons. If redundant cable pairs are not present, then each power utilization parameter would depend on just one conductor.

Preferably, the pairwise comparisons include detecting a fault in response to the condition:

$$|P_A - P_B| > c$$

where $P_A$ is the power utilization parameter of the first phase, $P_B$ is the power utilization parameter of the second phase, and c is a predetermined constant. Thus, if the absolute difference between the currents or voltages present in different phases is greater than the predetermined constant then a fault is detected. The magnitude of constant c is preferably selected to provide early detection of degrading conditions while avoiding false alarms. The occurrence of the fault is reported to the user so that it can be corrected. For completeness, the pairwise comparisons further include detecting a fault in response to the conditions:

$$|P_B - P_C| > c, \text{ and}$$

$$|P_A - P_C| > c$$

where $P_C$ is the power utilization parameter of the third phase.

The sequence for operating the motor as generated by the H-bridge inverter includes a continuous succession of respective cycles for all the phases. For purposes of the phase to phase comparisons, the power utilization parameters characterize the current or voltage measurement of each respective phase over at least one cycle. Measurement for one phase is conducted closely in time to the measurements for the other phases. To characterize any particular cycle, the measurement may be comprised of a peak-to-peak value or an RMS value, for example. When a power utilization parameter is comprised of current measurements then the currents within each respective conductor pair are preferably added together, and the resulting sum is used for the comparisons. When a power utilization parameter is comprised of voltage measurements then an average of the two voltages at the conductors within a respective conductor pair can be used.

What is claimed is:

1. A blood pump system for left ventricle assist comprising:
   an implantable pump unit having a multiphase brushless motor including windings for energizing according to first, second, and third phases;
   a subcutaneous cable having first, second, and third parallel pairs of redundant conductors, wherein the conductor pairs are connected to respective ends of the windings; and
   an external unit coupled to the cable, comprising:
      an H-bridge inverter having first, second, and third phase legs coupled to the first, second, and third conductor pairs, respectively;
      first and second pairs of power sensors responsive to electrical power in each of the redundant conductors in the first and second conductor pairs, respectively; and
      a controller coupled to the H-bridge inverter and the power sensors for 1) switching the H-bridge inverter in a sequence for operating the motor, 2) characterizing a first power utilization parameter of one of the conductor pairs during energization of the first phase, 3) characterizing a second power utilization parameter of one of the conductor pairs during energization of the second phase, 4) characterizing a third power utilization parameter of one of the conductor pairs during energization of the third phase, and 5) pairwise comparing the power utilization parameters and detecting a fault in the implantable pump in response to an imbalance of one of the comparisons;
      wherein the sequence is comprised of respective phase cycles, and wherein the power utilization parameters characterize a current or voltage measurement of a respective phase over at least one cycle.

2. The system of claim 1 wherein the power sensors are further comprised of a third pair responsive to electrical power in each of the redundant conductors in the third conductor pair, wherein the first power utilization parameter is characterized in response to electrical power sensed by the first sensor pair, wherein the second power utilization parameter is characterized in response to electrical power sensed by the second sensor pair, and wherein the third power utilization parameter is characterized in response to electrical power sensed by the third sensor pair.

3. The system of claim 1 wherein the pairwise comparisons include detecting a fault in response to the condition:

$$|P_A - P_B| > c$$

where $P_A$ is the power utilization parameter of the first phase, $P_B$ is the power utilization parameter of the second phase, and c is a predetermined constant.

4. The system of claim 3 wherein the pairwise comparisons further include detecting a fault in response to the condition:

$$|P_B - P_C| > c$$

where $P_C$ is the power utilization parameter of the third phase.

5. The system of claim 4 wherein the pairwise comparisons further include detecting a fault in response to the condition:

$$|P_A - P_C| > c.$$

6. The system of claim 1 wherein the measurement is a peak-to-peak value.

7. The system of claim 1 wherein the measurement is an RMS value.

8. The system of claim 1 wherein each power utilization parameter is comprised of current measurements including a sum of currents within each respective conductor pair.

9. The system of claim 1 wherein each power utilization parameter is comprised of voltage measurements including an average of voltages at each respective conductor pair.

10. A method for detecting faults in a blood pump system for left ventricle assist, wherein the blood pump system has an implantable pump unit having a multiphase brushless motor including windings for energizing according to first, second, and third phases, wherein the blood pump system has a subcutaneous cable having first, second, and third parallel pairs of redundant conductors, wherein the conductor pairs are connected to respective ends of the windings, wherein the blood pump system has an H-bridge inverter having first, second, and third phase legs coupled to the first, second, and third conductor pairs, respectively, wherein the blood pump system has first and second pairs of power sensors responsive to electrical power in each of the redundant conductors in the first and second conductor pairs, respectively, the method comprising the steps of:

switching the H-bridge inverter in a sequence for operating the motor;

characterizing a first power utilization parameter of one of the conductor pairs during energization of the first phase;

characterizing a second power utilization parameter of one of the conductor pairs during energization of the second phase;

characterizing a third power utilization parameter of one of the conductor pairs during energization of the third phase;

pairwise comparing the power utilization parameters; and detecting a fault in the implantable pump in response to an imbalance of one of the comparisons;

wherein the sequence for operating the motor is comprised of respective phase cycles, and wherein the power utilization parameters characterize a current or voltage measurement of a respective phase over at least one cycle.

11. The method of claim 10 wherein the pairwise comparisons include the condition:

$$|P_A - P_B| > c$$

where $P_A$ is the power utilization parameter of the first phase, $P_B$ is the power utilization parameter of the second phase, and c is a predetermined constant.

12. The method of claim 11 wherein the pairwise comparisons further include the condition:

$$|P_B - P_C T| > c$$

where $P_C$ is the power utilization parameter of the third phase.

13. The method of claim 12 wherein the pairwise comparisons further include the condition:

$$|P_A - P_C| > c.$$

14. The method of claim 10 wherein the measurement is a peak-to-peak value.

15. The method of claim 10 wherein the measurement is an RMS value.

16. The method of claim 10 wherein each power utilization parameter is comprised of current measurements including a sum of currents within each respective conductor pair.

17. The method of claim 10 wherein each power utilization parameter is comprised of voltage measurements including an average of voltages at each respective conductor pair.

* * * * *